US009671418B2

(12) United States Patent
Mellars et al.

(10) Patent No.: US 9,671,418 B2
(45) Date of Patent: Jun. 6, 2017

(54) MULTIPLE PAYLOAD TYPE CARRIER

(71) Applicant: Siemens Healthcare Diagnostics Inc., Tarrytown, NY (US)

(72) Inventors: Colin Mellars, Dover, NJ (US); Baris Yagci, Whippany, NJ (US); Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/760,100

(22) PCT Filed: Jan. 10, 2014

(86) PCT No.: PCT/US2014/011007
§ 371 (c)(1),
(2) Date: Jul. 9, 2015

(87) PCT Pub. No.: WO2014/110346
PCT Pub. Date: Jul. 17, 2014

(65) Prior Publication Data
US 2015/0355211 A1 Dec. 10, 2015

Related U.S. Application Data

(60) Provisional application No. 61/751,619, filed on Jan. 11, 2013.

(51) Int. Cl.
*G01N 35/04* (2006.01)
*G01N 35/00* (2006.01)
(Continued)

(52) U.S. Cl.
CPC ............ *G01N 35/04* (2013.01); *G01N 35/00* (2013.01); *G01N 35/02* (2013.01); *B65G 17/002* (2013.01);
(Continued)

(58) Field of Classification Search
CPC ............... B65G 17/002; E21B 19/146; G01N 2035/00801; G01N 2035/0406;
(Continued)

(56) References Cited

U.S. PATENT DOCUMENTS 3,696,946 A  10/1972  Hunter et al.
5,941,366 A * 8/1999  Quinlan ............... B65G 17/002
                                                  198/465.1
(Continued)

FOREIGN PATENT DOCUMENTS

EP    0 931 259 B1    11/2006
EP    0931259 B1 *   11/2006 .......... B01J 19/0046

OTHER PUBLICATIONS

PCT International Search Report and Written Opinion dated Jul. 8, 2014 (11 Pages).

*Primary Examiner* — Jennifer Wecker

(57) ABSTRACT

An automation system for use with in vitro diagnostics includes a track configured to provide one or more paths and a plurality of payload carriers having payload carrier types. One or more of the plurality of payload carrier types has a different payload carrier dimension in a direction of travel than another payload carrier type. The system includes a plurality of carriers configured to move along the track in the direction of travel. Each of the plurality of carriers has a substantially identical carrier dimension in the direction of travel and configured to hold any one of the plurality of payload carrier types. The system includes a controller configured to navigate the plurality of carriers along the track based on at least one of: (i) the substantially identical carrier dimension in the direction of travel; and (ii) one or more of the different payload carrier dimensions in the direction of travel.

15 Claims, 17 Drawing Sheets

(51) Int. Cl.
*G01N 35/02* (2006.01)
*G01N 35/10* (2006.01)
*B65G 17/00* (2006.01)
*E21B 19/14* (2006.01)

(52) U.S. Cl.
CPC ...... *E21B 19/146* (2013.01); *G01N 35/00732* (2013.01); *G01N 35/026* (2013.01); *G01N 2035/00207* (2013.01); *G01N 2035/00801* (2013.01); *G01N 2035/0401* (2013.01); *G01N 2035/042* (2013.01); *G01N 2035/0406* (2013.01); *G01N 2035/0412* (2013.01); *G01N 2035/0422* (2013.01); *G01N 2035/0467* (2013.01); *G01N 2035/0493* (2013.01); *Y10T 436/113332* (2015.01)

(58) Field of Classification Search
CPC ........... G01N 2035/0467; G01N 35/04; G01N 35/00; G01N 35/02; G01N 35/026; G01N 35/0401; G01N 35/0412; G01N 35/042; G01N 35/0422
See application file for complete search history.

(56) References Cited

U.S. PATENT DOCUMENTS

| | | | |
|---|---|---|---|
| 6,808,021 B2 | 10/2004 | Zimmerman et al. | |
| 7,591,630 B2* | 9/2009 | Lert, Jr. | B65G 1/0492 414/279 |
| 2002/0040783 A1* | 4/2002 | Zimmerman | B63G 8/001 166/366 |
| 2004/0134750 A1* | 7/2004 | Luoma, II | B01L 9/00 198/340 |
| 2006/0051239 A1* | 3/2006 | Massaro | B01L 9/06 422/63 |

* cited by examiner

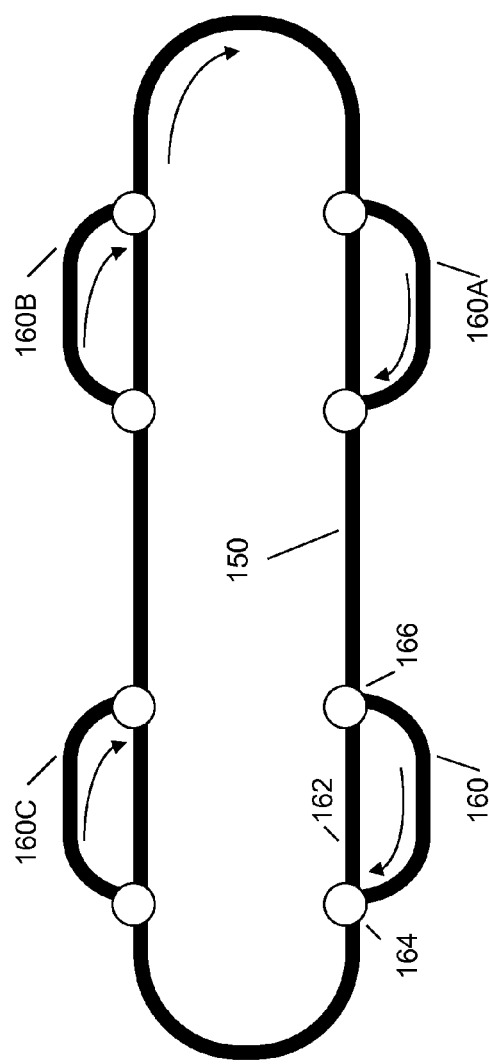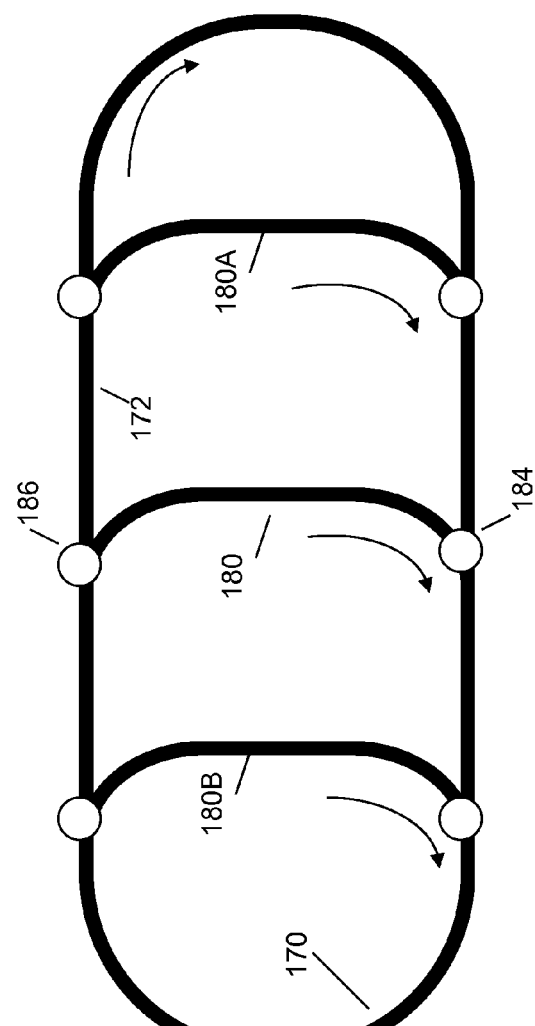

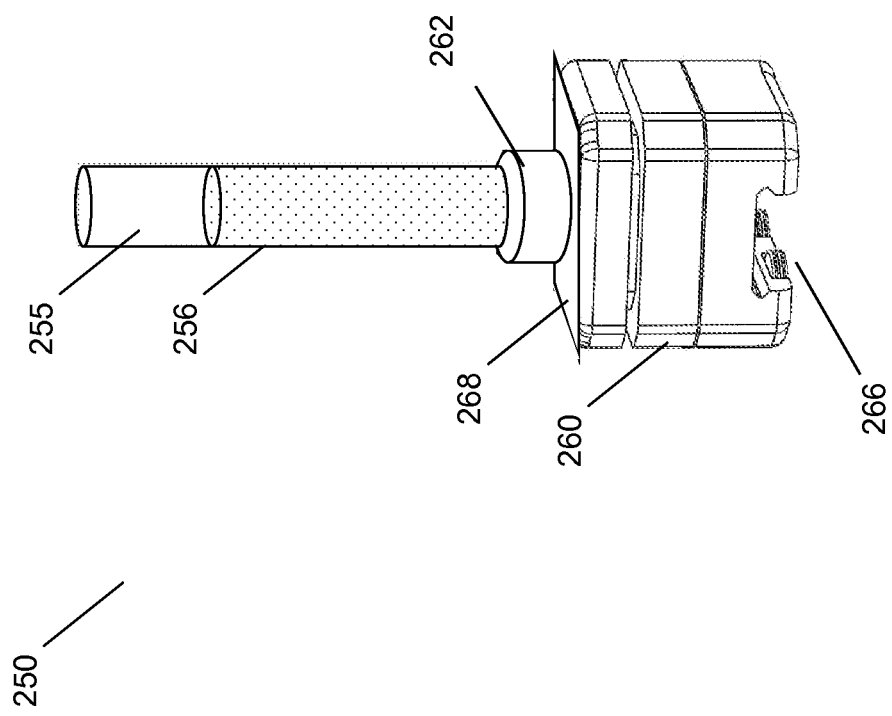

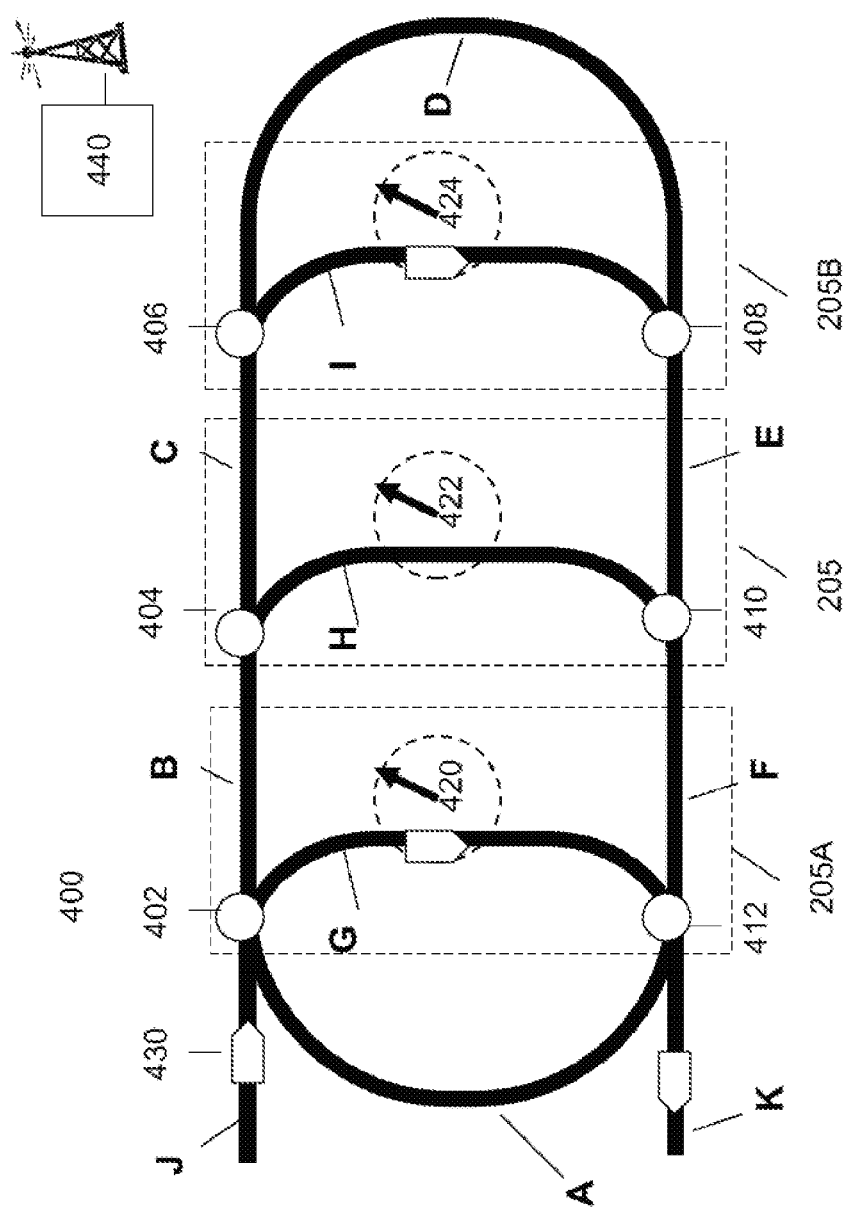

MULTIPLE PAYLOAD TYPE CARRIER

CROSS-REFERENCE TO RELATED APPLICATIONS

This application claims priority to U.S. provisional application Ser. No. 61/751,619 filed Jan. 11, 2013, which is incorporated herein by reference in its entirety.

TECHNOLOGY FIELD

The present invention relates in general to an automation system for use in a laboratory environment and, more particularly, to systems and methods for transporting objects of different geometries for in vitro diagnostics in a clinical analyzer.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available.

In some conventional IVD automation systems, single objects, typically individual carrier mechanisms (carriers), sometimes called pucks, or racks carrying payloads are shuttled between different stations. These conventional systems include track guidance mechanisms (e.g. track widths, singulating gates, interface gates, and diverting gates) and propulsion mechanisms designed around the particular shapes and sizes (geometries) of the puck or payload carried by the puck to reduce the size, complexity and cost of the systems. Accordingly, these conventional systems are not designed to carry payload types having different geometries (e.g. sample tubes and reagent wedges) along a single lane of a track without incurring navigational problems, such as collisions, blocked lanes and difficulty maneuvering turns.

SUMMARY

Embodiments of the present invention include an automation system for use with in vitro diagnostics that includes a track configured to provide one or more paths and a plurality of payload carriers that includes payload carrier types. One or more payload carrier types has a different payload carrier dimension in a direction of travel than another payload carrier type. The automation system also includes a plurality of carriers configured to move along the track in the direction of travel. Each of the plurality of carriers has a substantially identical carrier dimension in the direction of travel and is configured to hold any one of the plurality of payload carrier types. The automation system further includes a controller configured to navigate the plurality of carriers along the track based on at least one of: (i) the substantially identical carrier dimension in the direction of travel; and (ii) one or more of the different payload carrier dimensions in the direction of travel.

According to one embodiment, each of the plurality of carriers is configured to move along a single lane of the track in the direction of travel.

According to another embodiment, the controller is configured to navigate the plurality of carriers along the track based on a plurality of effective carrier dimensions in the direction of travel. Each effective carrier dimension is equal to the larger of: (i) the substantially identical carrier dimension in the direction of travel; and (ii) the corresponding payload carrier dimension in the direction of travel.

In one embodiment, the automation system further includes carrier exclusion zones. Each carrier exclusion zone includes an area having: (i) an exclusion zone length dimension extending past opposite sides of a corresponding carrier in the direction of travel; and (ii) an exclusion zone width dimension extending perpendicular to the direction of travel. Each exclusion zone length dimension in the direction of travel is: (i) based on the largest effective carrier dimension in the direction of travel and (ii) greater than the largest effective carrier dimension in the direction of travel. The controller is further configured to navigate the plurality of carriers along the track based on the exclusion zone length dimension in the direction of travel.

According to an aspect of an embodiment, the effective carrier dimensions in the direction of travel and the carrier exclusion zones in the direction of travel are determined by the controller.

According to one embodiment, each corresponding exclusion zone length dimension in the direction of travel is based on each corresponding effective carrier dimension in the direction of travel. The controller is further configured to navigate the plurality of carriers along the track based on the corresponding exclusion zone length dimensions in the direction of travel.

In one embodiment, the controller is further configured to navigate the plurality of carriers along the track based on minimum distances between the one or more carriers. The minimum distances are determined by at least one of (i) a speed of the one or more carriers, (ii) a velocity of the one or more carriers, (iii) a mass of the one or more carriers; (iv) a maximum breaking force provided by the track; and (v) a maximum breaking force provided by the one or more carriers.

In another embodiment, the automation system further includes one or more sensors configured to sense: (i) the carrier dimension in the direction of travel; and (ii) one or more of the different payload carrier dimensions in the direction of travel.

According to an aspect of an embodiment, at least one carrier of the plurality of carriers comprises the one or more sensors.

According to one embodiment, the one or more sensors is configured to observe (i) the carrier dimension in the direction of travel; and (ii) one or more of the different payload carrier dimension in the direction of travel.

In an aspect of an embodiment, at least one carrier of the plurality of carriers comprises an onboard processor. In another aspect, the at least one carrier further comprises a transceiver configured to communicate with the onboard processor and the controller.

According to one embodiment, the automation system further includes a plurality of electromagnetic coils in at least one of the track and the plurality of carriers and a plurality of magnets in at least one of the other of the track and the plurality of carriers. The plurality of electromagnetic coils and the plurality of magnets are configured to propel the plurality of carriers along the track.

Embodiments of the present invention include a carrier for transporting fluid samples in an in vitro diagnostics environment that include a carrier body configured to move along a track in a direction of travel. The carrier body has carrier dimensions that include a carrier dimension in the direction of travel. The carrier also includes a mounting interface coupled to the carrier body and configured to hold either one of: (i) a first type of payload carrier having a first payload carrier dimension in the direction of travel and a first payload carrier dimension perpendicular to the first payload carrier dimension in the direction of travel; and (ii) a second type of payload carrier having a second payload carrier dimension in the direction of travel and a second payload carrier dimension perpendicular to the second payload carrier dimension in the direction of travel. The first payload carrier dimension in the direction of travel and the second payload carrier dimension in the direction of travel are different.

According to one embodiment, the carrier further includes one or more sensors configured to sense: (i) another carrier body dimension in the direction of travel; and (ii) one or more of the different payload carrier dimensions in the direction of travel.

In one embodiment, the onboard processor is configured to navigate the carrier body along the track based on at least one of: (i) the carrier dimension in the direction of travel; (ii) the first payload carrier dimension in the direction of travel; and (iii) the second payload carrier dimension in the direction of travel.

In another embodiment, the carrier further includes a communications system configured to receive routing instructions to navigate the carrier body along the track based on at least one of: (i) the carrier dimension in the direction of travel; (ii) the first payload carrier dimension in the direction of travel; and (iii) the second payload carrier dimension in the direction of travel.

In one aspect of an embodiment, the carrier is configured to be propelled along the track via magnetic forces.

Embodiments of the present invention include a method for operating an in vitro diagnostics system that includes holding a plurality of payload carrier types having dimensions different from each other with a plurality of carriers having substantially the same carrier dimensions and moving the plurality of carriers along a track in a direction of travel. The method also includes navigating the plurality of carriers along the track based on at least one of: (i) a carrier dimension in the direction of travel; and (ii) one or more of the payload carrier dimensions in the direction of travel.

In one embodiment, navigating the plurality of carriers along the track includes navigating the plurality of carriers based on an effective carrier dimension that is equal to the larger of: (i) the corresponding carrier dimension in the direction of travel; and (ii) the corresponding payload carrier dimension in the direction of travel.

In another embodiment, the method further includes determining carrier exclusion zone dimensions in the direction of travel adjacent to the plurality of carriers based on the largest effective carrier dimension in the direction of travel. The navigating further includes navigating the plurality of carriers along the track based on the exclusion zone length dimensions in the direction of travel.

In an aspect of an embodiment, the method further includes determining carrier exclusion zone dimensions in the direction of travel adjacent to each of the plurality of carriers based on each corresponding effective carrier dimension in the direction of travel. The navigating further includes navigating the plurality of carriers along the track based on each corresponding exclusion zone length dimension in the direction of travel.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

FIG. 6 is a diagrammatic view of exemplary routes in an exemplary track configuration that can be used for navigation of sample carriers in certain embodiments;

Figure 1:
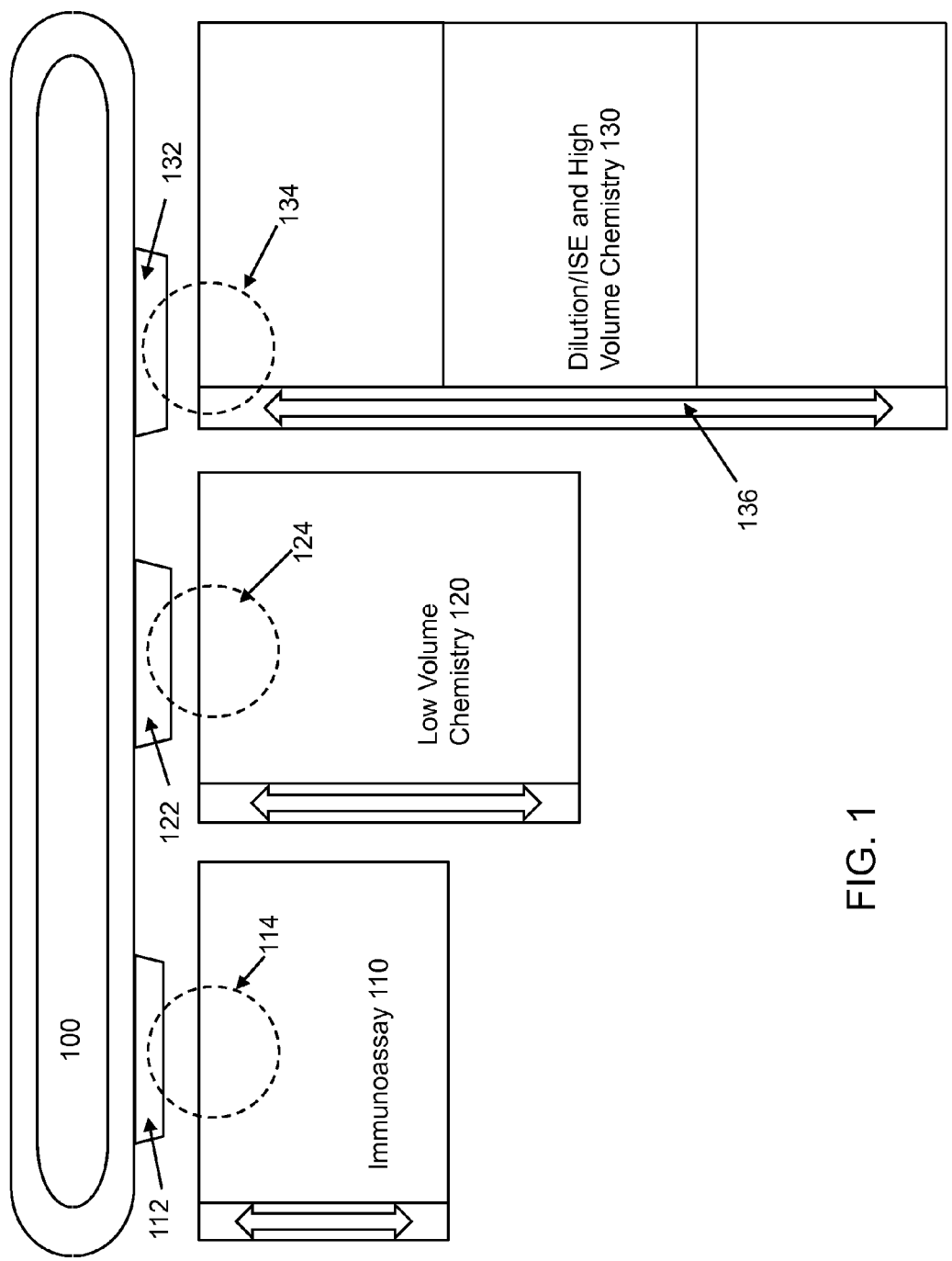
FIG. 1 is a top view of an exemplary clinical analyzer geometry that can be improved by use of the automation system embodiments disclosed.

DETAILED DESCRIPTION OF ILLUSTRATIVE EMBODIMENTS TERMS AND CONCEPTS ASSOCIATED WITH SOME EMBODIMENTS

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary System

An exemplary track geometry, for use in transporting payloads, such as sample tubes within an analyzer typical in prior art configurations, is shown in FIG. 1. As used herein, an analyzer can refer to any automated system or preparing or testing properties of patient samples in an automated manner. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carrier, as used herein, is a general term for pucks, trays, or the like for handling material in accordance with the disclosed embodiments. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
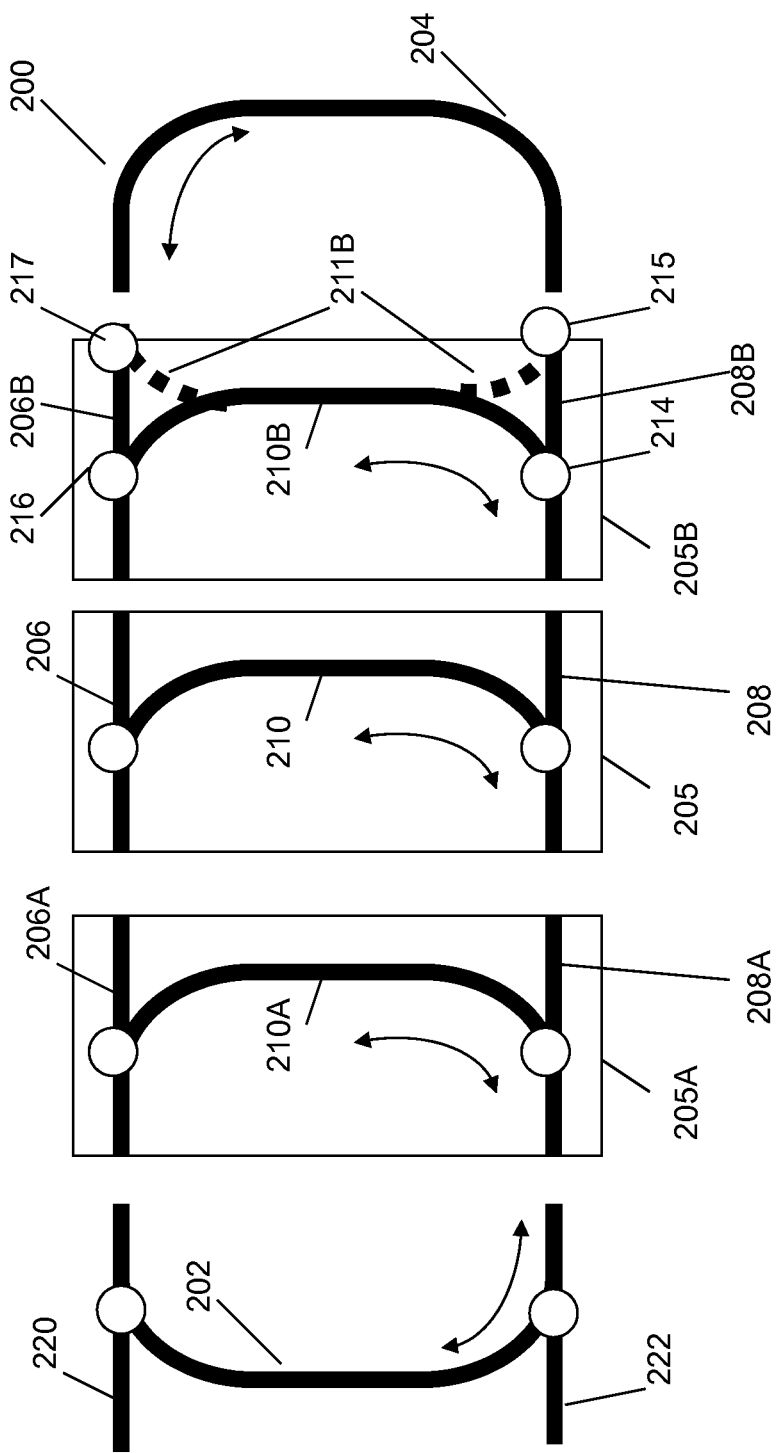
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module a prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200.

When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components described herein. The main body 260 supports a bracket 262, which can accept a payload. In some embodiments, such as a sample tube, this is a shallow hole (slot) that is designed to accept a fluid container 255, such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
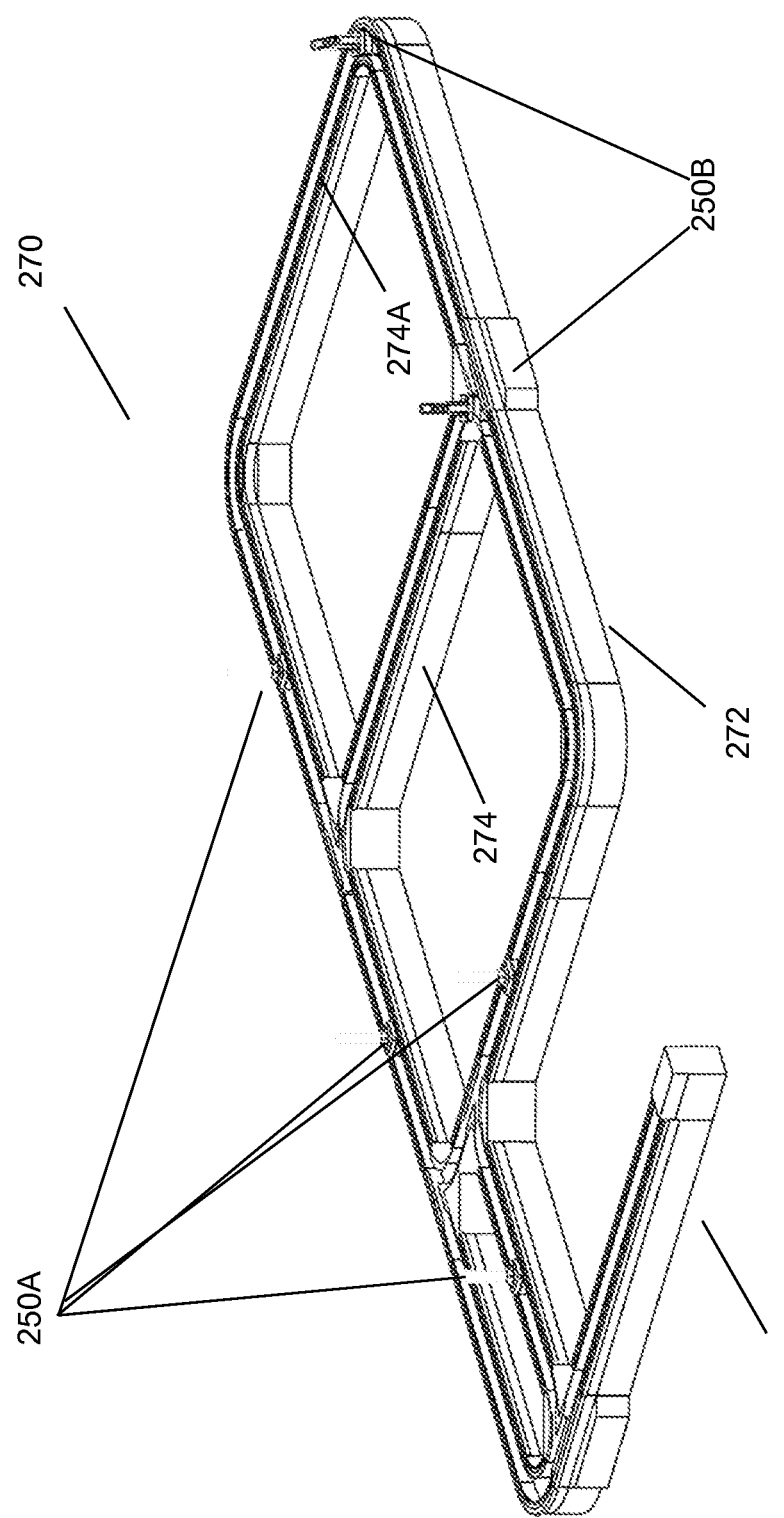
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
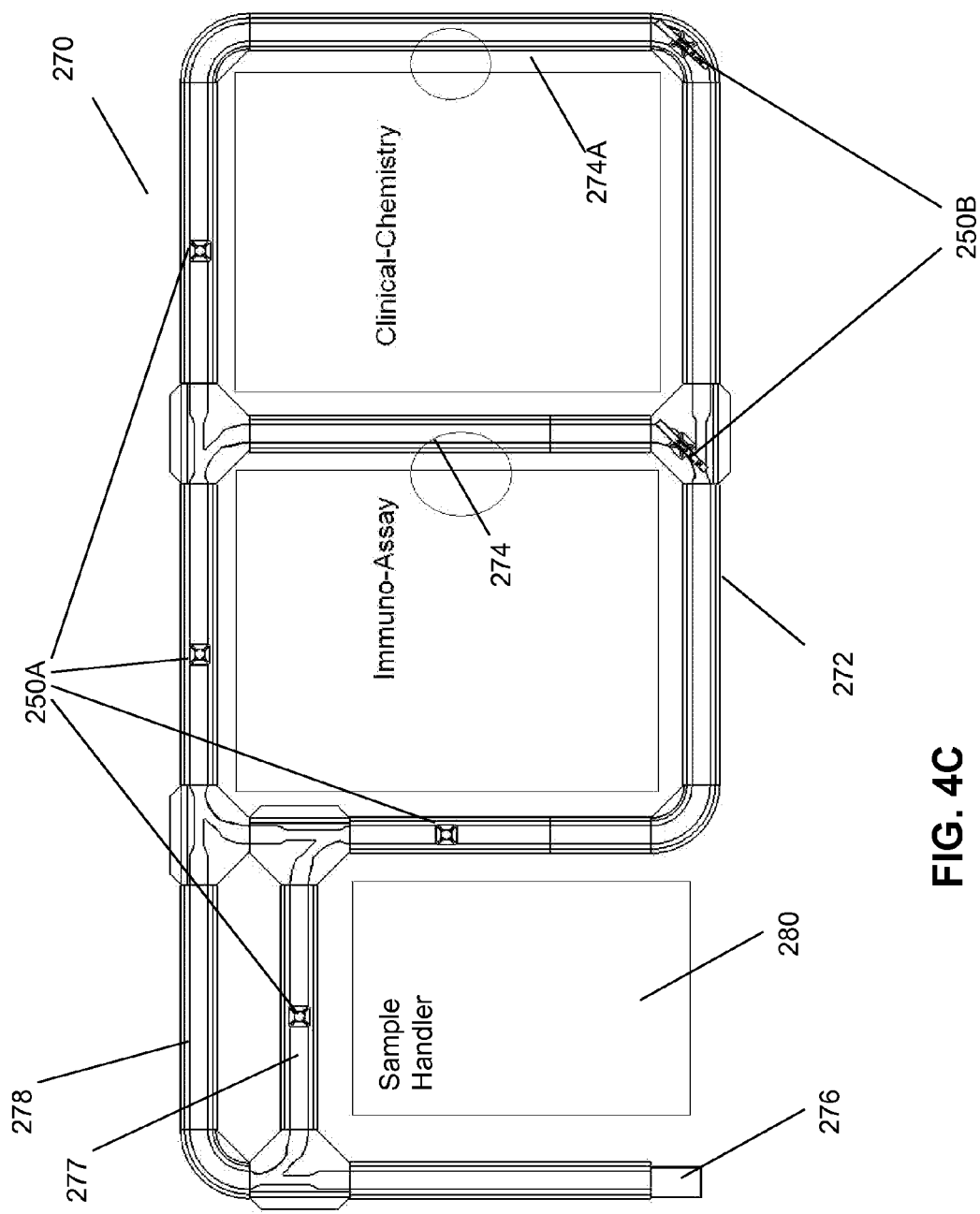
FIG. 4C is a top view of an exemplary automation system that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas some embodiments may utilize passive pucks or trays (e.g., the puck is a simple plastic or rubber brick that lacks active or autonomous systems, power, onboard processing, or control) to reduce cost and complexity, in some embodiments the added complexity and cost necessary to integrate intelligence and autonomy into individual carriers (which can include smart pucks or trays in some embodiments) can provide certain benefits. Accordingly, embodiments of the present invention can utilize intelligent carriers to enable certain improvements over passive pucks on the friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as a communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and an image sensor that can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
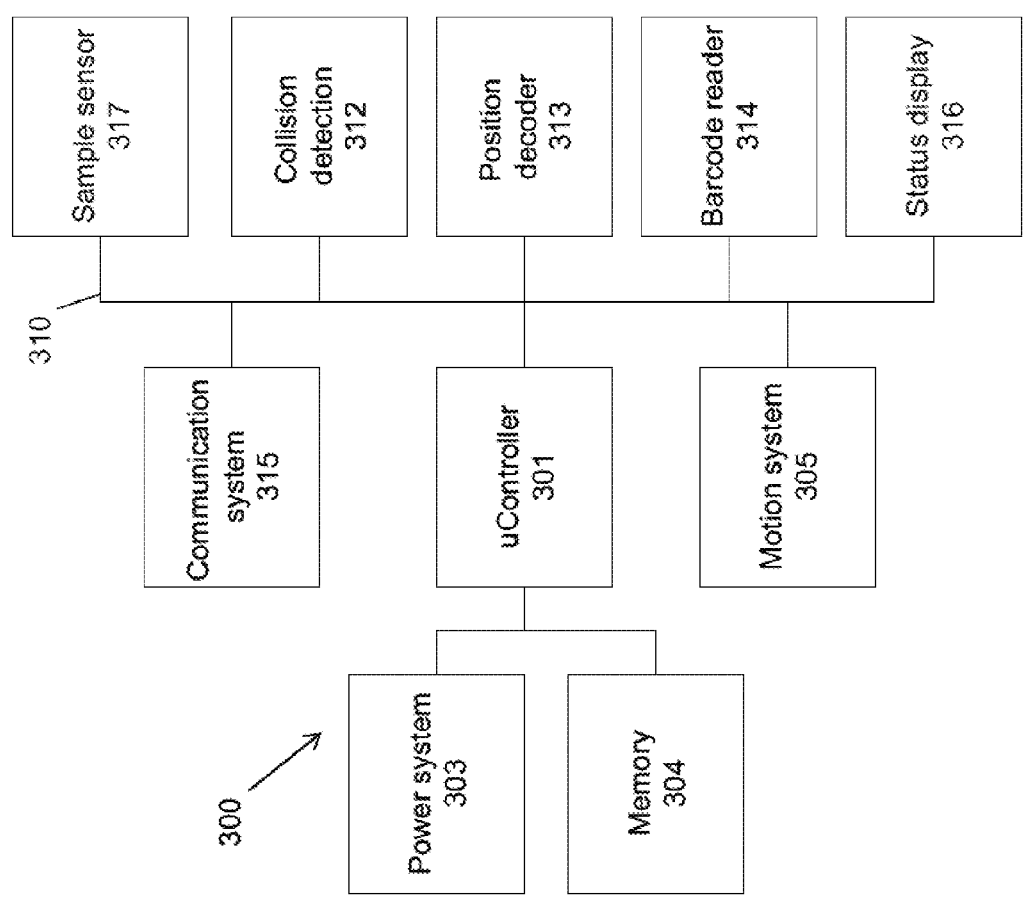
FIG. 5 is a system block diagram of the control systems including onboard active carriers that can be used with certain embodiments disclosed herein.

FIG. 5 shows a top-level system diagram of the control systems and sensors for an exemplary intelligent autonomous carrier 300. Carrier 300 can be any suitable embodiment of a carrier, such as a carrier 250, shown at FIG. 4A, that is configured to hold a single fluid container 255 and carrier 700, shown at FIG. 7A to FIG. 9B, that is configured to hold different payload carrier types, such as reagent wedge 702 (shown at FIG. 7B) and sample tube carrier 704 (shown at FIG. 7C). Carrier 300 is controlled by an onboard processor, such as microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates while, in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

FIG. 6 shows an exemplary routing scenario in automation track system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Carrier 430 can be any suitable embodiment of a carrier, such as carrier 300, shown in FIG. 5 and carrier 500, shown at FIG. 9A to FIG. 9D. Central management processor 440 uses the status information of the carriers and track as well as the identity of samples or other payload carried by the carriers and the required assays to be performed by the system on these samples.

The exemplary track 400 shown in FIG. 6 includes a first curve segment A, that connects to straight segment B and a pullout segment G, (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 6, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random access queues. For example, once carrier 430 stops on section G, additional instructions can be conveyed via central management processor 440 or directly from analyzer 205A to the carrier 430 via RF transmission or other means, such as local optical or inductive/near-field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1.

By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J.

Multiple Payload Type Carrier and Anti-Collision System

While carriers have thus far been often described with respect to transporting samples, it should be understood that carriers are not limited to those that transport samples (e.g. sample carriers). The same mechanisms described with respect to transporting samples may also be used to provide maintenance services to the automation system and the analyzer itself. Traffic on the track 710 of the automation system can include a variety of types of payload carriers, such as sample carriers (e.g. sample tubes), maintenance carriers, reagent delivery carriers (e.g. reagent wedges), and the like. Some payload carrier types may have substantially the same geometries as other payload types, but may be different from the other payload types because they have mechanical features configured to hold a different type of material (e.g. reagents, patient samples). For example, a reagent pack and a 5-position sample tube rack may have substantially the same size and shape, but have different mechanical features to hold stabilize their respective payloads. One or more payload carrier types may also be different from another payload type because they may have different dimensions than another payload carrier type.

While some conventional systems may include pucks designed to carry different sizes of the same type of payload (e.g. different sized sample tubes), these conventional systems are not designed to carry payload types having different geometries along a single lane 706 of a track 710 without incurring navigational problems. For example, larger payloads (e.g. reagent wedges) may have difficulty navigating (e.g. maneuvering turns and gates) the same lane of a track 710 designed around a precise geometry of a smaller payload (e.g. sample tube). Accordingly, conventional systems may only transport pucks or racks having the same or similar geometry and are only capable of carrying a single payload type along the same lane of the track 710.

Figure 7A:
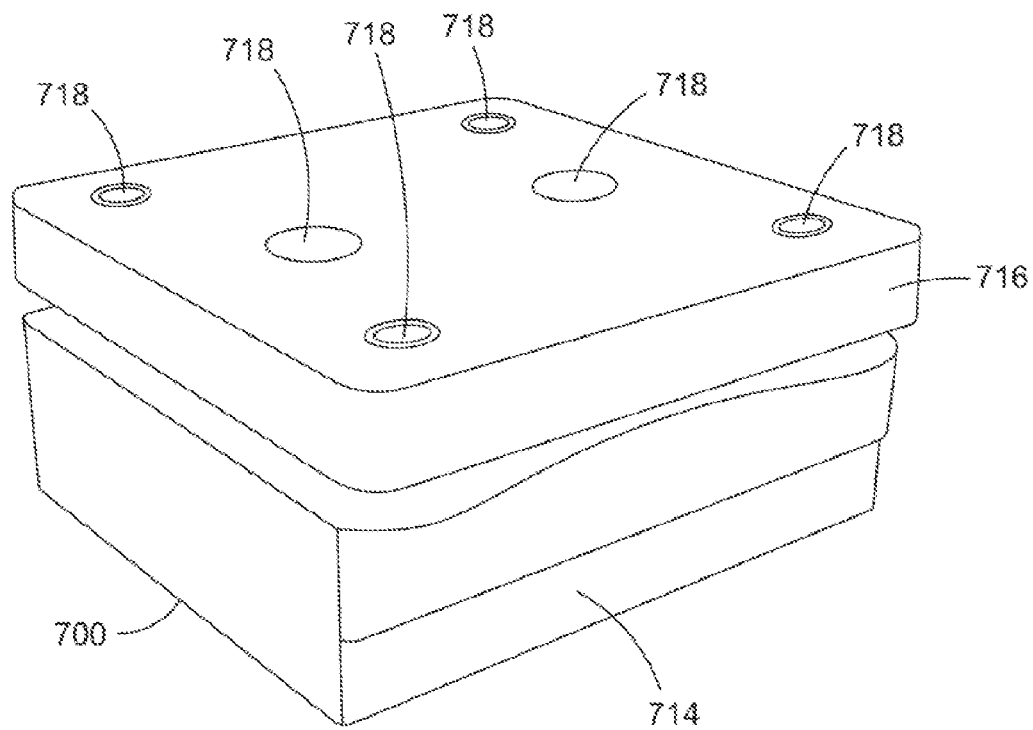
FIG. 7A is a perspective view of an exemplary carrier configured to hold different payload carrier types that can be used with the embodiments disclosed herein.

Embodiments of the invention include improved systems and methods for moving different payload types (e.g. sample tubes and reagents containers) along a single lane 706 of a track, such as tracks 710. FIG. 7A is a perspective view of an exemplary generic carrier 700 configured to hold different payload carrier types, such as reagent wedge 702 (shown at FIG. 7B) and sample tube carrier 704 (shown at FIG. 7C).

As shown at FIG. 7A, carrier 700 includes a carrier body 714, which can house internal electronic components described herein, and a mounting interface, such as mounting plate 716 coupled to the carrier body 714. Different payload carrier types, such as a reagent wedge 702 and sample tube carrier 704 may be mounted to mounting plate 716. In some embodiments, these payload carrier types 702 and 704 may be mounted to mounting plate 716 via threaded mounting holes 718. In some embodiments, payload carrier types 702 and 704 may be mounted in different ways, such as mechanically and magnetically, via different types of mounting interfaces such as brackets, plates, recesses, holes, adhesives and magnets.

Figure 7B:
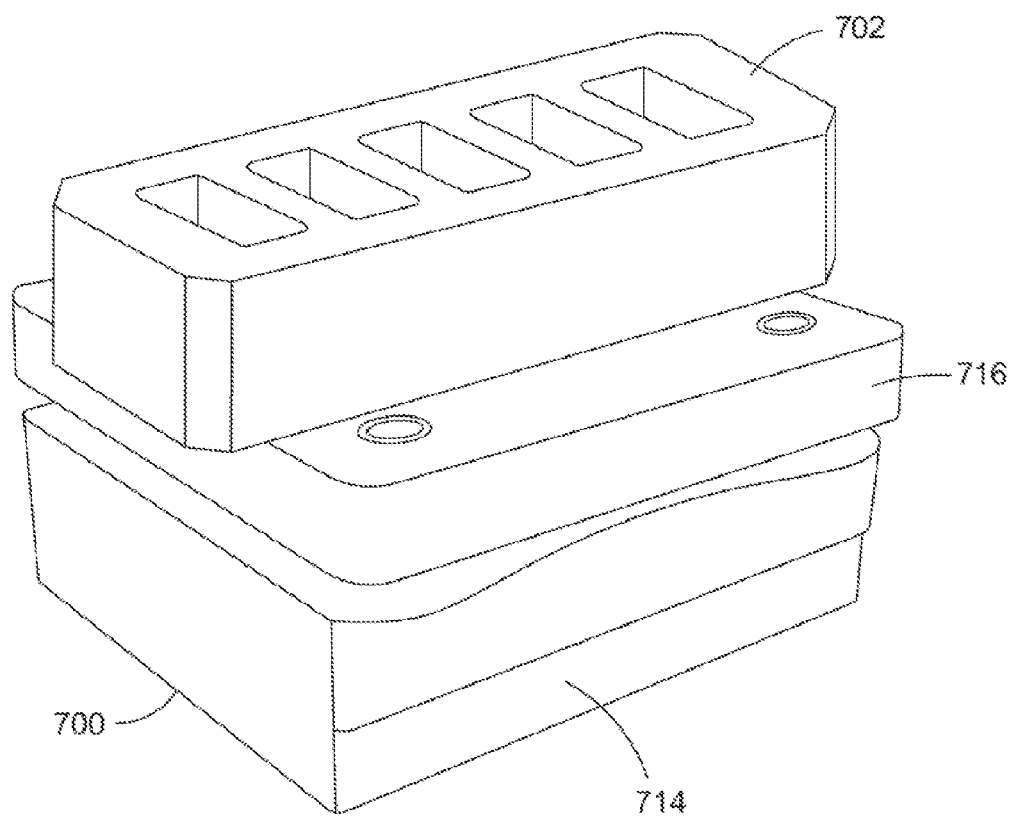
FIG. 7B is a perspective view of the exemplary carrier shown at FIG. 7A holding a reagent wedge carrier that can be used with the embodiments disclosed herein.
Figure 7C:
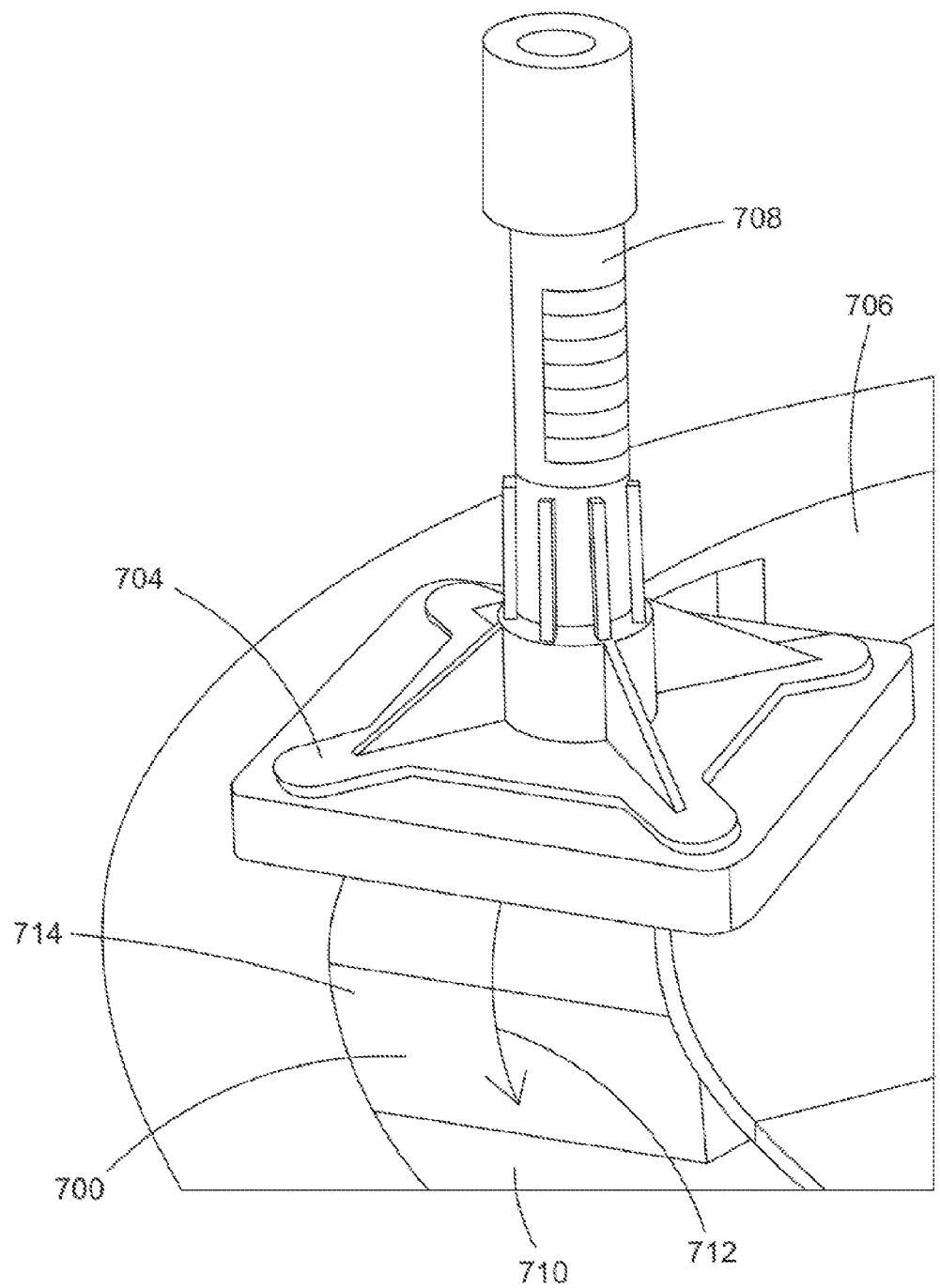
FIG. 7C is a perspective view of an exemplary carrier shown at FIG. 7A holding a sample tube carrier that can be used with the embodiments disclosed herein.

FIG. 7B shows exemplary carrier 700 holding a reagent wedge carrier 702 configured to hold a reagent (not shown). FIG. 7C shows exemplary carrier 700 holding a sample tube carrier 704, which in turn holds a sample tube 708 containing a fluid sample, such as blood or urine. FIG. 7C also shows carrier 700 moving sample tube carrier 704 along a single lane 706 of the track 710 in a direction of travel 712. Although not shown, carrier 700 may move other payload carrier types, such as reagent wedge 702 along the same lane 706 of track 710 in the direction of travel 712. Accordingly, a more efficient lab automation system compressed to a single lane may be used to move different types of payloads.

The dimensions of generic carrier 700 illustrated in the embodiments herein are exemplary. Other embodiments may include a generic carrier of any size or shape that is configured to move different payload carrier types along a single lane 706 of a track 710. In some embodiments, carrier 700 may be a passive carrier. In other embodiments, carrier 700 may be an intelligent or autonomous carrier that includes one or more of the components shown at FIG. 5 and described herein.

Figure 8A:
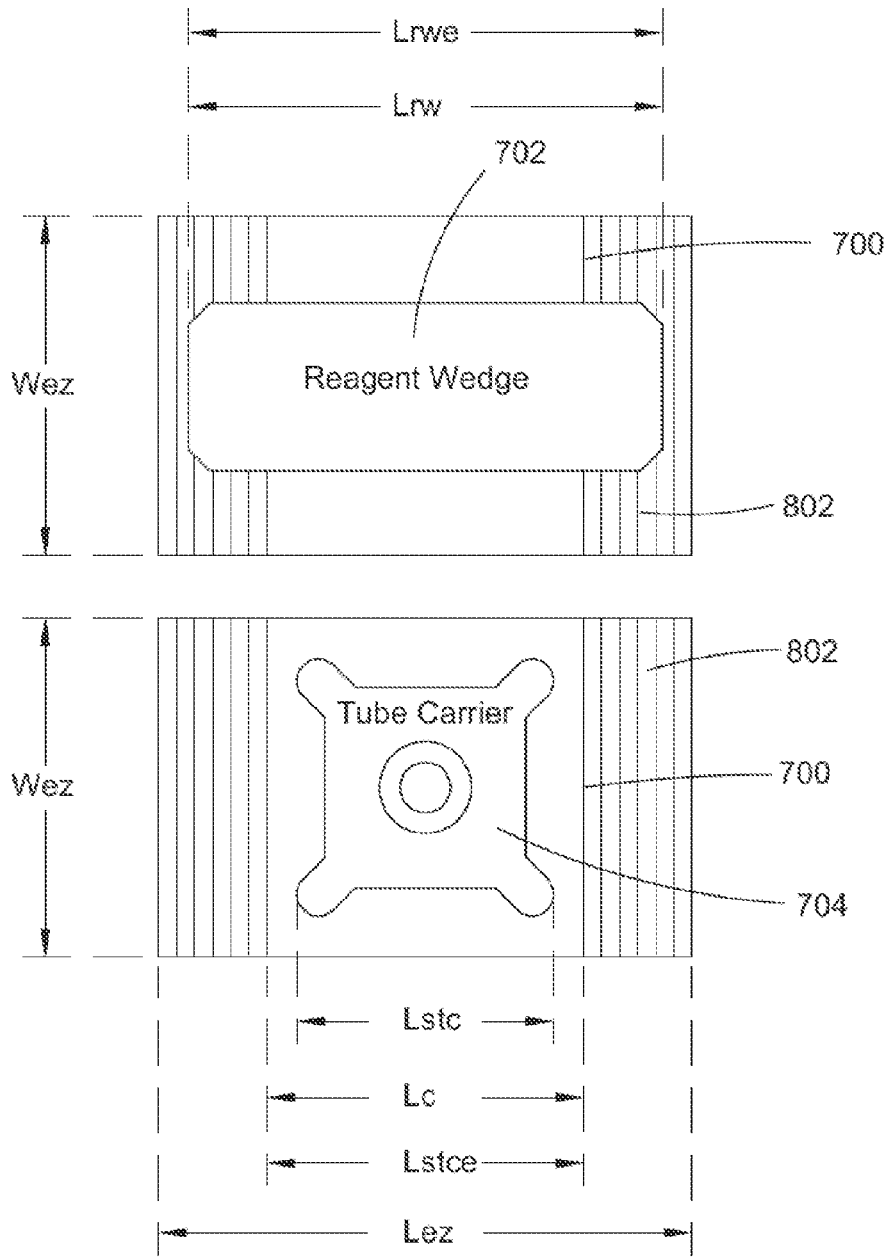
FIG. 8A is a top view of a reagent wedge mounted on a generic carrier and a sample tube carrier mounted on an adjacent generic carrier illustrating common exclusion zone dimensions that can be used with the embodiments disclosed herein.

Some embodiments may include an anti-collision system to reduce impacts to carriers and payload carriers. FIG. 8A is a top view of a reagent wedge 702 mounted on carrier 700 and a sample tube carrier 704 mounted on an adjacent carrier 700. FIG. 8A illustrates differing length dimensions L of carrier 700, reagent wedge 702 and sample tube carrier 704. For example, generic carrier 700 has a carrier length dimension Lc. Reagent wedge 702 is mounted on generic carrier 700 and has a reagent wedge length dimension Lrw that is larger than carrier length dimension Lc. Sample tube carrier 704 mounted on adjacent generic carrier 700 has a sample tube carrier length dimension Lstc that is smaller than the carrier length dimension Lc. These length dimensions L may be used by a controller/processor, such as central management processor 440, local or sub-controllers (not shown) and onboard processor 301, to determine precise locations of the carriers 700 and payload carriers 702, 704 to navigate the carriers 700 holding the payload carriers 702, 704 along a single lane 706 of the track 710.

Figure 8B:
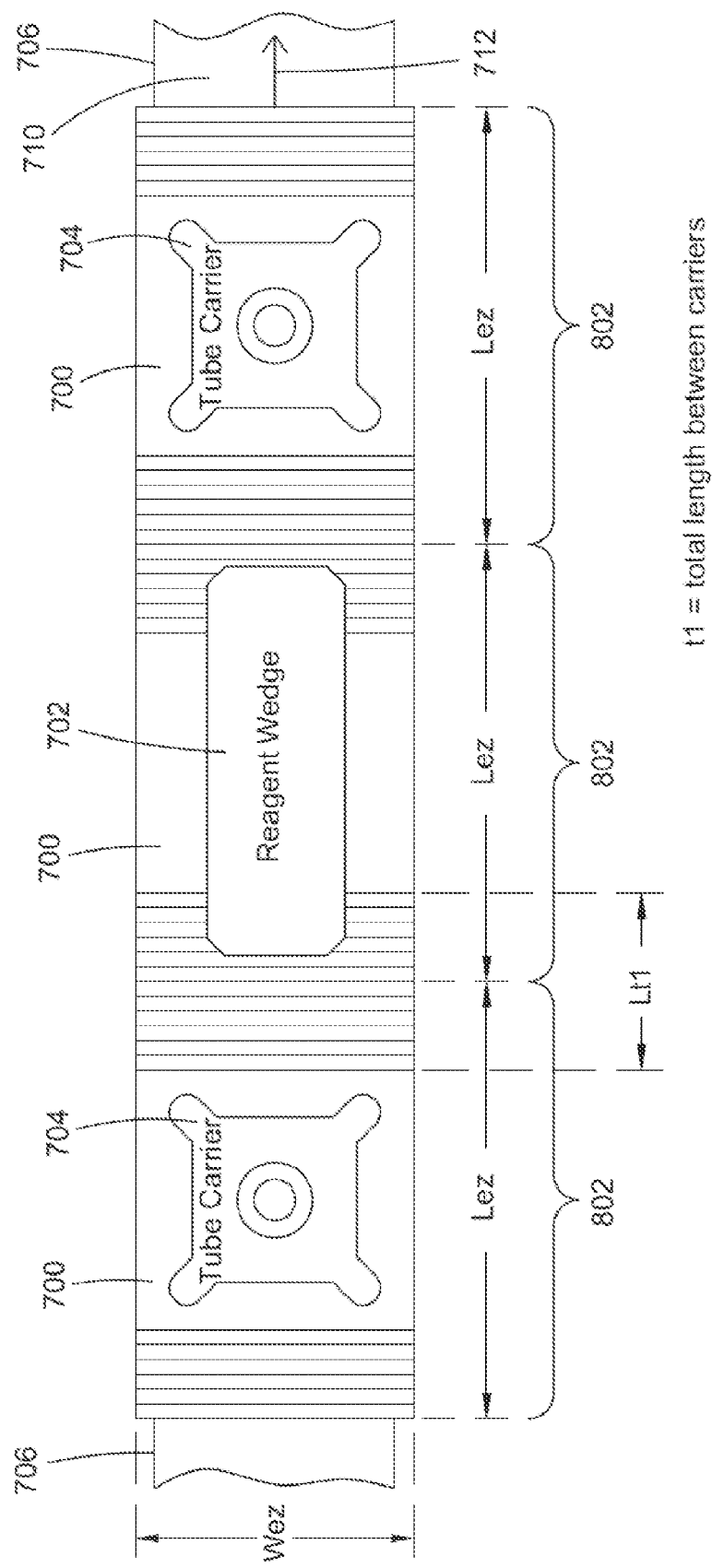
FIG. 8B is a top view of different payload carriers mounted on generic carriers with common exclusion zone dimensions moving in a direction of travel along a track that can be used with the embodiments disclosed herein.

FIG. 8B shows a configuration of the different payload carriers 702, 704 mounted on generic carriers 700 (shown at FIG. 8A) and moving in a direction of travel 712 along track 710. In some embodiments, a controller 440, 301 may be configured to navigate the plurality of carriers 700 along the track 710 based on the carrier length dimension Lc in the direction of travel 712 and one or more of the different payload carrier length dimensions Lrw and Lstc in the direction of travel 712. For example, in the embodiment shown at FIG. 8B, the lengths Lc, Lrw and Lstc corresponding to the carrier 700 and payload carriers 702, 704 are respective dimensions in the direction of travel 712.

In some embodiments, the controller 440, 301 may navigate the carriers 700 based on a determined effective carrier length dimension Le for each of the carriers. For example, as shown at FIG. 8A, the effective carrier length dimension for a respective carrier 700 is equal to the larger of: (i) the carrier length dimension Lc in the direction of travel 712; and (ii) the corresponding payload carrier length dimension (Lrw and Lstc) in the direction of travel 712. For the carrier 700 and corresponding reagent wedge 702 shown at the top of FIG. 8A, the effective carrier length dimension Lrwe may be determined to be equal to the reagent wedge length dimension Lrw because it is larger than the carrier length dimensions Lc. For the carrier 700 and corresponding sample tube carrier 704 shown at the bottom of FIG. 8A, the effective carrier length dimension Lstce may be determined to be equal to the generic carrier length dimension Lc, because it is larger than the sample tube carrier length dimensions Lstc.

In some embodiments, the controller 440, 301 may navigate the carriers 700 along the track 710 based on exclusion zones 802 adjacent the carriers 700. As shown at FIG. 8A and FIG. 8B, each carrier 700 includes a corresponding exclusion zone 802. Each carrier exclusion zone 802 includes an area having an exclusion zone length dimension Lez extending in the direction of travel 712 and an exclusion zone width dimension Wez extending perpendicular to the direction of travel. Each exclusion zone length dimension Lez extends past opposite sides of a corresponding carrier 700 in the direction of travel 712.

In some embodiments, the dimensions of the exclusion zones for each generic carrier are not dependent on the dimensions of each corresponding payload carrier type. Rather, dimensions in the direction of travel 712 for each of the exclusion zones 802 are the same and are based on the largest effective carrier dimension in the direction of travel 712. For example, as shown at FIG. 8A and FIG. 8B, each exclusion zone length dimension Lez is the same and is determined to be greater than the largest effective carrier dimension Lrwe. In some aspects, the exclusion zone length dimension Lez may be determined to be a fixed offset (e.g. 5 cm) greater than the largest effective length dimension. In other aspects, the exclusion zone length dimension Lez may be determined to be other functions of the largest effective length dimension, such as a percentage (e.g. 30%) larger than the largest effective length dimension Le.

In some embodiments, the exclusion zone length dimension Lez of the exclusion zones 802 may be dynamically determined along the track 710. For example, in one aspect, a new payload carrier, having the largest effective carrier dimension, enters the track 710 or a segment of the track 710, the exclusion zone length dimension Lez may be dynamically changed to be equal the effective carrier dimension of the new payload carrier. In another aspect, the exclusion zone length dimension Lez may be dynamically changed based on a minimum following distance of a carrier. The minimum following distance may be determined based on one or more variables, such as the speed of one or more carriers, the mass of one or more carriers and the maximum breaking force that can be provided by the track or carrier itself. A controller 440, 301 may then navigate the plurality of carriers along the track 710 based on the exclusion zone length dimension Lez in the direction of travel.

As described above, in the embodiments shown at FIGS. 8A and 8B, each of the exclusion zones 802 include the same dimensions and are based on the generic carrier having largest effective carrier dimension. In the embodiments shown at FIG. 9A and FIG. 9B, the dimensions of the exclusion zones 902A and 902B for each generic carrier 700 are based on the dimensions of each corresponding payload carrier type. That is, the dimensions of the exclusion zones 902A and 902B for each generic carrier 700 are based on an effective carrier dimension for each corresponding generic carrier 700.

Figure 9A:
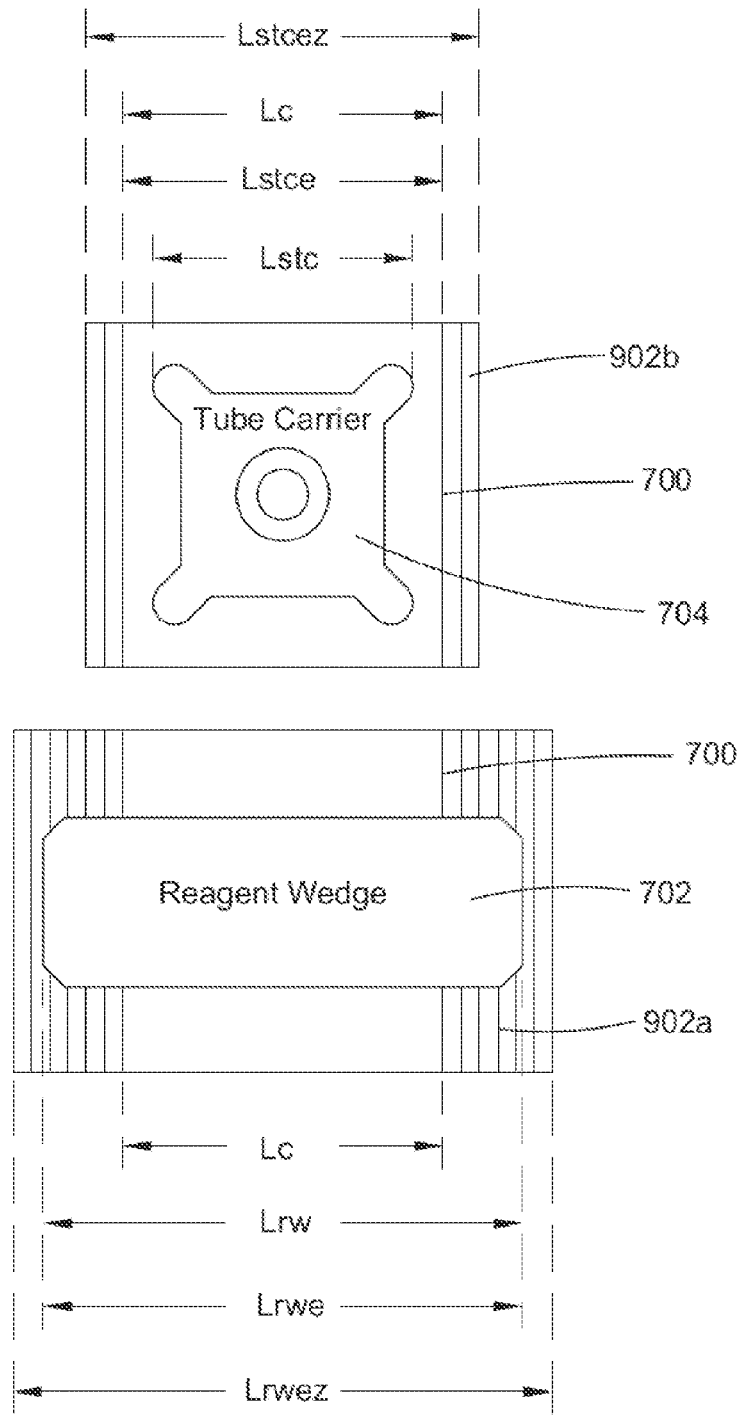
FIG. 9A is a top view of a reagent wedge mounted on a generic carrier and a sample tube carrier mounted on an adjacent generic carrier illustrating different exclusion zone dimensions that can be used with the embodiments disclosed herein.
Figure 9B:
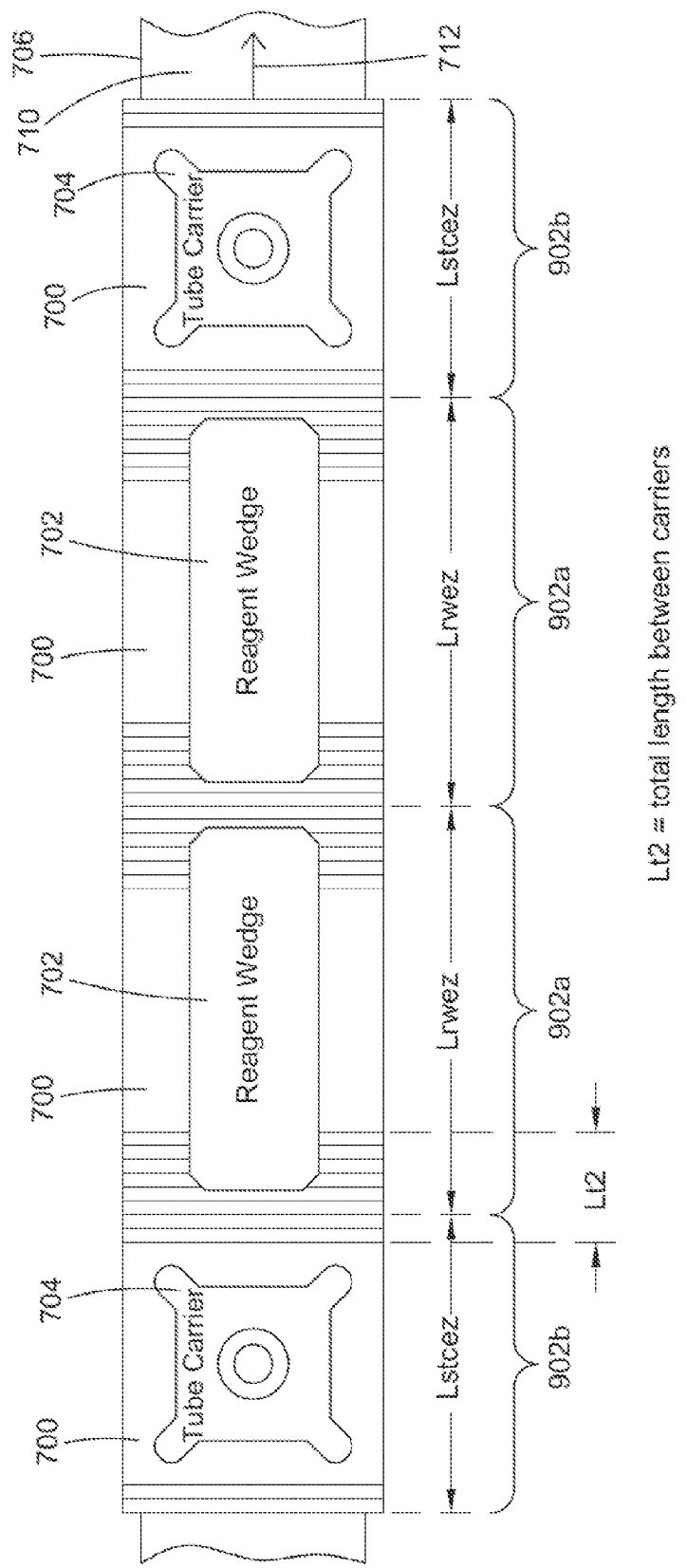
FIG. 9B is a top view of different payload carriers mounted on generic carriers with different exclusion zone dimensions moving in a direction of travel along a track that can be used with the embodiments disclosed herein.

The effective carrier dimensions in the embodiments shown at FIGS. 9A and 9B are determined the same way as the effective carrier dimensions in the embodiments shown at FIGS. 8A and 8B. Accordingly, for the carrier 700 and corresponding reagent wedge 702 shown at the bottom of FIG. 9A, the effective carrier length dimension Lrwe may be determined to be equal to the reagent wedge length dimension Lrw because it is larger than the carrier length dimensions Lc. For the carrier 700 and corresponding sample tube carrier 704 shown at the top of FIG. 9A, the effective carrier length dimension Lstce may be determined to be equal to the generic carrier length dimension Lc, because it is larger than the sample tube carrier length dimensions Lstc.

In contrast to the common exclusion zone length dimensions Lez in the direction of travel 712 for the exclusion zones 802 shown at FIG. 8A and FIG. 8B, the exclusion zone length dimensions Lrwez and Lstcez in the direction of travel 712 of the respective exclusion zones 902a and 902b shown at FIG. 9A and FIG. 9B are based on the corresponding effective carrier length dimensions Lrwe and Lstce. That is, the exclusion zone length dimension Lrwez of exclusion zone 902a is based on the effective carrier length dimension Lrwe of the carrier 700 and corresponding reagent wedge carrier 702 shown at the bottom of FIG. 9A. The exclusion zone length dimension Lstcez of exclusion zone 902b is based on the effective carrier length dimension Lstce of the carrier 700 and corresponding sample tube carrier 704 shown at the top of FIG. 9A. As shown at FIG. 9A, the exclusion zone length dimension Lrwez is larger than the exclusion zone length dimension Lstcez. A controller 440, 301 may then navigate the carriers 700 along the track 710 based on each corresponding exclusion zone length dimensions in the direction of travel 712.

Tailoring the dimensions of the exclusion zones 802 for each generic carrier 700 to the dimensions of each corresponding payload carrier type may provide a more efficient use of space along the track 710. For example, comparing FIG. 8B to FIG. 9B, the total length Lt1 (shown at FIG. 8B) between a carrier 700 holding a sample tube carrier 704 and a carrier 700 holding a reagent wedge carrier 702 is larger than the total length Lt2 (shown at FIG. 9B) between a carrier 700 holding a sample tube carrier 704 and a carrier 700 holding a reagent wedge carrier 702. Accordingly, less space is needed between the carrier 700 holding sample tube carrier 704 and the reagent wedge 702, while still maintaining a buffer area to avoid collisions between the carrier 700 holding sample tube carrier 704 and the reagent wedge 702.

In some aspects, the central controller 440 may be configured to determine the carrier exclusion zones 802 adjacent the carriers 700. In other aspects, the controller 440 may receive an indication of the corresponding exclusion zone length dimensions Lez in the direction of travel 712 and navigate the carriers 700 along the track 710 and prevent collisions between the carriers 700 and the payload carriers 702, 704 based on the corresponding exclusion zone length dimensions in the direction of travel 712. In some aspects, the central controller 440 may transmit the determined exclusion zones 802 to a local controller (not shown) or the onboard processor 301. The local controller (not shown) or the onboard processor 301 may then navigate the carriers 700 along the track 710 based on the determined exclusion zones 802. In other aspects, local controller (not shown) or the onboard processor 301 may determine the carrier exclusion zones 802 adjacent the carriers 700.

In some embodiments, one or more sensors may be used to sense location information and/or dimensional information, such as one or more carrier dimensions in the direction of travel and one or more of the different payload carrier dimensions in the direction of travel. The sensors may transmit the location information and/or dimensional information to a central controller 440, one or more local controllers (not shown) or the onboard processor 301 for navigating the carriers 700 along the track 710. Exemplary sensors may include IR range-finding, magnetic sensors, microwave sensors, or optical detectors.

The carriers 700 may be autonomous and include onboard processing and sensor capabilities. For example, onboard sensors 312, 313 and 314 in an autonomous carrier 700 may sense location information and/or dimensional information. Communication system 315 may include a transceiver to transmit information, such as the sensed location information and/or dimensional information to the onboard processor 301 for navigating the autonomous carrier 700 along the track 710. In some aspects, the transceiver may transmit information to the central controller 440 which may transmit the determined exclusion zones 802 to one or more local controllers.

In some embodiments, one or more sensors (not shown) may be used to observe location information and/or dimensional information, such as carrier dimensions in the direction of travel; and one or more of the different payload carrier dimension in the direction of travel. The sensors along the track 710 may include Hall effect sensors or cameras that can determine the position of individual carriers and relay this information to the carrier. The sensors may transmit the location information and/or dimensional information to a central controller 440, one or more local controllers (not shown) or the onboard processor 301 for navigating the carriers 700 along the track 710.

Figure 10:
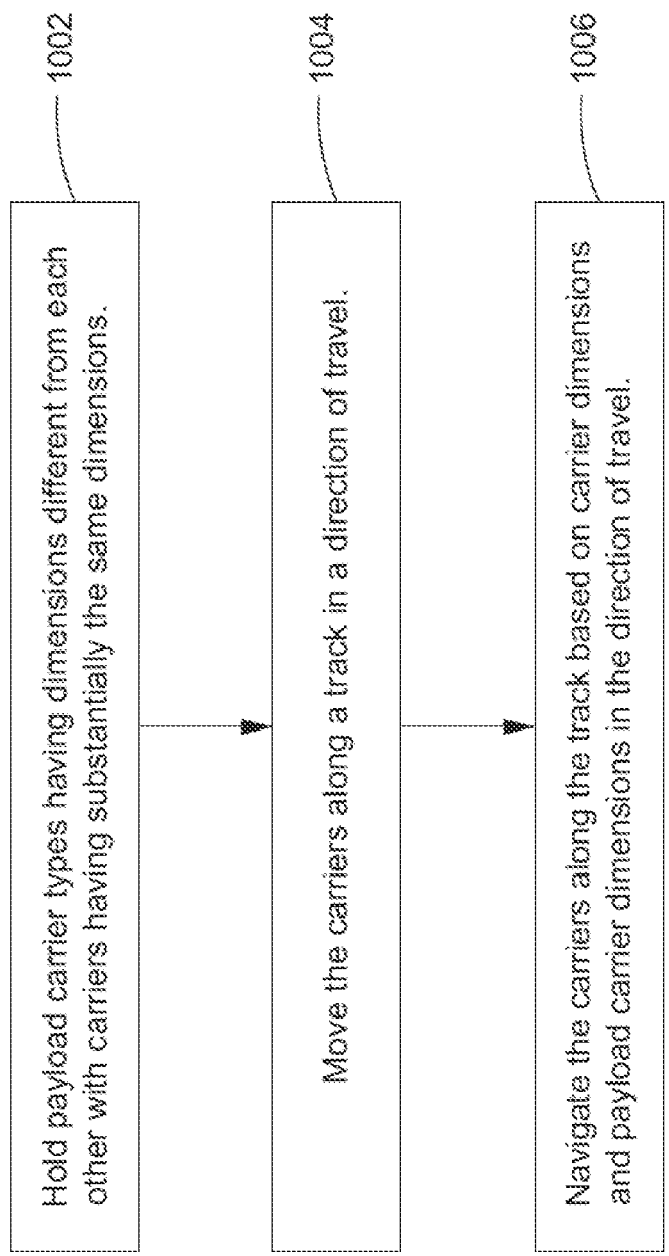
FIG. 10 is a flow diagram illustrating a method for operating an in vitro diagnostics system that can be used with the embodiments disclosed herein.

FIG. 10 is a flow diagram illustrating a method for operating an in vitro diagnostics system that can be used with the embodiments disclosed herein. At block 1002, genetic carriers 700 having substantially the same dimensions may be used to hold payload carrier types 702, 704 having dimensions different from each other. At block 1004, the carriers 700 may be moved along a track 710 in a direction of travel 712. At block 1106, the plurality of carriers may be navigated along the track based on at least one of: (i) a carrier dimension in the direction of travel; and (ii) one or more of the payload carrier dimensions in the direction of travel.

Figure 11:
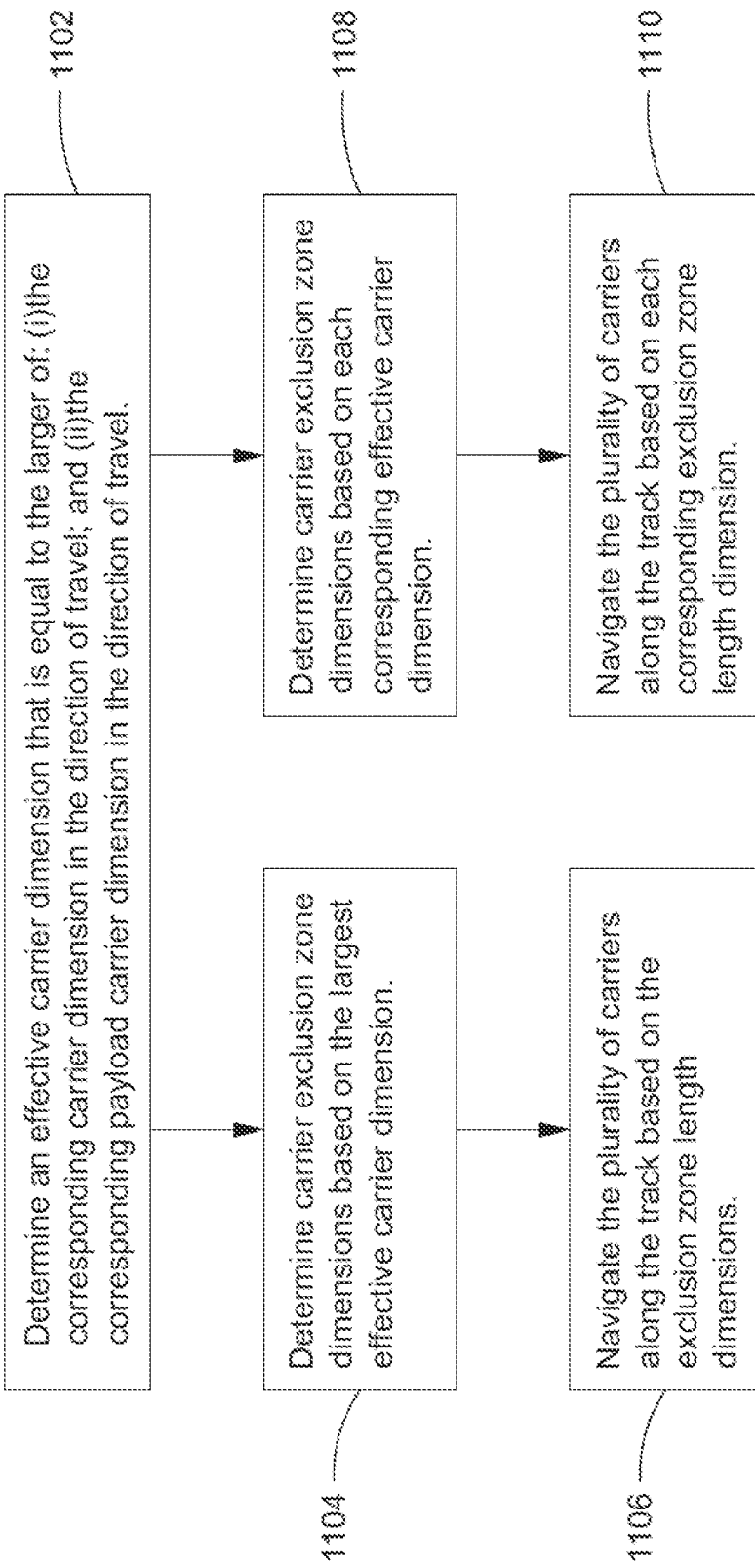
FIG. 11 is a flow diagram illustrating a method for navigating carriers along a track based on carrier dimensions and payload carrier dimensions that can be used with the embodiments disclosed herein.

FIG. 11 is a flow diagram illustrating a method for navigating carriers along a track based on carrier dimensions and payload carrier dimensions shown at block 1006 at FIG. 10. At block 1102, an effective carrier dimension is determined that is equal to the larger of: (i) the corresponding carrier dimension in the direction of travel; and (ii) the corresponding payload carrier dimension in the direction of travel. For example, for the carrier 700 and corresponding reagent wedge 702 shown at the bottom of FIG. 9A, the effective carrier length dimension Lrwe may be determined to be equal to the reagent wedge length dimension Lrw because it is larger than the carrier length dimensions Lc. For the carrier 700 and corresponding sample tube carrier 704 shown at the top of FIG. 9A, the effective carrier length dimension Lstce may be determined to be equal to the generic carrier length dimension Lc, because it is larger than the sample tube carrier length dimensions Lstc.

The path shown at blocks 1104 and 1106 describe embodiments in which the dimensions Lez of the exclusion zones 802 for each generic carrier 700 are not dependent on the dimensions of each corresponding payload carrier type 702, 704. As shown at block 1104, carrier exclusion zone dimensions Lez in the direction of travel may be determined to be adjacent to the plurality of carriers 700 based on the largest effective carrier dimension in the direction of travel. For example, as shown at FIG. 8A and FIG. 8B, each exclusion zone length dimension Lez is the same and is determined to be greater than the largest effective carrier dimension Lrwe. At block 1106, the generic carriers 700 may be navigated along the track 710 based on the exclusion zone length dimensions Lez in the direction of travel 712.

The path shown at blocks 1108 and 1110 describe embodiments in which the dimensions of the exclusion zones 802 for each generic carrier 700 are based on the dimensions of each corresponding payload carrier type 702, 704. As shown at block 1108, carrier exclusion zone dimensions in the direction of travel are determined to be adjacent to each of the plurality of carriers 700 based on each corresponding effective carrier dimension in the direction of travel. For example, the exclusion zone length dimension Lrwez of exclusion zone 902a is based on the effective carrier length dimension Lrwe of the carrier 700 and corresponding reagent wedge carrier 702 shown at the bottom of FIG. 9A. The exclusion zone length dimension Lstcez of exclusion zone 902b is based on the effective carrier length dimension Lstce of the carrier 700 and corresponding sample tube carrier 704 shown at the top of FIG. 9A. At block, 1110, the plurality of carriers may be navigated along the track based on each corresponding exclusion zone length dimension in the direction of travel.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system for use with in vitro diagnostics comprising:
    a track configured to provide one or more paths;
    a plurality of payload carriers comprising a plurality of payload carrier types, one or more of the plurality of payload carrier types having a different payload carrier dimension in a direction of travel than another payload carrier type;
    a plurality of carriers configured to move along the track in the direction of travel, each of the plurality of carriers having a substantially identical carrier dimension in the direction of travel and configured to hold any one of the plurality of payload carrier types;
    carrier exclusion zones, each carrier exclusion zone comprising an area having: (i) an exclusion zone length dimension extending past opposite sides of a corresponding carrier in the direction of travel; and (ii) an exclusion zone width dimension extending perpendicular to the direction of travel, wherein each exclusion zone length dimension in the direction of travel is: (i) based on a largest effective carrier dimension in the direction of travel and (ii) greater than the largest effective carrier dimension in the direction of travel; and
    a controller configured to navigate the plurality of carriers along the track based on at least one of: (i) the substantially identical carrier dimension in the direction of travel; and (ii) one or more of the different payload carrier dimensions in the direction of travel; further based on a plurality of effective carrier dimensions in the direction of travel, wherein each effective carrier dimension is equal to the larger of: (i) the substantially identical carrier dimension in the direction of travel; and (ii) the corresponding payload carrier dimension in the direction of travel; and further based on the exclusion zone length dimension in the direction of travel;
    wherein the effective carrier dimensions in the direction of travel and the carrier exclusion zones in the direction of travel are determined by the controller.

2. The automation system of claim 1, wherein each of the plurality of carriers is configured to move along a single lane of the track in the direction of travel.

3. The automation system of claim 1, wherein each corresponding exclusion zone length dimension in the direction of travel is based on each corresponding effective carrier dimension in the direction of travel, and
    the controller is further configured to navigate the plurality of carriers along the track based on the corresponding exclusion zone length dimensions in the direction of travel.

4. The automation system of claim 1, wherein the controller is further configured to navigate the plurality of carriers along the track based on minimum distances between the one or more carriers, the minimum distances determined by at least one of (i) a speed of the one or more carriers, (ii) a velocity of the one or more carriers, (iii) a mass of the one or more carriers; (iv) a maximum breaking force provided by the track; and (v) a maximum breaking force provided by the one or more carriers.

5. The automation system of claim 1, further comprising one or more sensors configured to sense: (i) the carrier dimension in the direction of travel; and (ii) one or more of the different payload carrier dimensions in the direction of travel.

6. The automation system of claim 5, wherein at least one carrier of the plurality of carriers comprises the one or more sensors.

7. The automation system of claim 5, wherein the one or more sensors is configured to observe (i) the carrier dimension in the direction of travel; and (ii) one or more of the different payload carrier dimension in the direction of travel.

8. The automation system of claim 1, wherein at least one carrier of the plurality of carriers comprises an onboard processor.

9. The automation system of claim 8, wherein the at least one carrier further comprises a transceiver configured to communicate with the onboard processor and the controller.

10. The automation system of claim 1, further comprising:
    a plurality of electromagnetic coils in at least one of the track and the plurality of carriers; and
    a plurality of magnets in at least one of the other of the track and the plurality of carriers,
    wherein the plurality of electromagnetic coils and the plurality of magnets are configured to propel the plurality of carriers along the track.

11. A carrier for transporting fluids in an in vitro diagnostics environment comprising:

a carrier body configured to move along a track in a direction of travel, the carrier body having carrier dimensions comprising a carrier dimension in the direction of travel; and a mounting interface coupled to the carrier body and configured to hold either one of:
  (i) a first type of payload carrier having a first payload carrier dimension in the direction of travel and a first payload carrier dimension perpendicular to the first payload carrier dimension in the direction of travel; and
  (ii) a second type of payload carrier having a second payload carrier dimension in the direction of travel and a second payload carrier dimension perpendicular to the second payload carrier dimension in the direction of travel;

wherein the first payload carrier dimension in the direction of travel and the second payload carrier dimension in the direction of travel are different:

wherein an onboard processor is configured to navigate the carrier body along the track based on at least one of: (i) the carrier dimension in the direction of travel; (ii) the first payload carrier dimension in the direction of travel; and (iii) the second payload carrier dimension in the direction of travel; further based on a plurality of effective carrier dimensions in the direction of travel, wherein each effective carrier dimension is equal to the larger of: (i) the first payload carrier dimension in the direction of travel; (ii) the second payload carrier dimension in the direction of travel; and (iii) the corresponding payload carrier dimension in the direction of travel; and further based on an exclusion zone length dimension in the direction of travel;

wherein a carrier exclusion zone comprises an area having: (i) an exclusion zone length dimension extending past opposite sides of a corresponding carrier in the direction of travel; and (ii) an exclusion zone width dimension extending perpendicular to the direction of travel, wherein each exclusion zone length dimension in the direction of travel is: (i) based on a largest effective carrier dimension in the direction of travel and (ii) greater than the largest effective carrier dimension in the direction of travel; and wherein the effective carrier dimensions in the direction of travel and the carrier exclusion zones in the direction of travel are determined by the onboard processor.

12. The carrier of claim 11, further comprising one or more sensors configured to sense: (i) another carrier body dimension in the direction of travel; and (ii) one or more of the different payload carrier dimensions in the direction of travel.

13. The carrier of claim 11, further comprising a communications system configured to receive routing instructions to navigate the carrier body along the track.

14. The carrier of claim 11, wherein the carrier is configured to be propelled along the track via magnetic forces.

15. A method for operating an in vitro diagnostics system, comprising:
  holding a plurality of payload carrier types having dimensions different from each other with a plurality of carriers having substantially the same carrier dimensions;
  moving the plurality of carriers along a track in a direction of travel;
  determining carrier exclusion zone dimensions in the direction of travel adjacent to the plurality of carriers based on a largest effective carrier dimension in the direction of travel, each carrier exclusion zone comprising an area having: (i) an exclusion zone length dimension extending past opposite sides of a corresponding carrier in the direction of travel; and (ii) an exclusion zone width dimension extending perpendicular to the direction of travel, wherein each exclusion zone length dimension in the direction of travel is: (i) based on the largest effective carrier dimension in the direction of travel and (ii) greater than the largest effective carrier dimension in the direction of travel; and
  navigating the plurality of carriers along the track based on at least one of: (i) a carrier dimension in the direction of travel; and (ii) one or more of the payload carrier dimensions in the direction of travel; further based on a plurality of effective carrier dimensions in the direction of travel, wherein each effective carrier dimension is equal to the larger of: (i) the substantially identical carrier dimension in the direction of travel; and (ii) the corresponding payload carrier dimension in the direction of travel; and further based on the exclusion zone length dimension in the direction of travel;
  wherein the effective carrier dimensions in the direction of travel and the carrier exclusion zones in the direction of travel are determined by a controller.

* * * * *